United States Patent
Liu et al.

(10) Patent No.: US 6,440,420 B1
(45) Date of Patent: Aug. 27, 2002

(54) **METHOD FOR EXTRACTING OLEAGINOUS SUBSTANCES FROM GERMINATION-ACTIVATED *GANODERMA LUCIDUM* SPORES**

(76) Inventors: Xin Liu; Xiao-Ni Huang, both of Building No. 391, 135 Xingang Xi Road, Guangzhou (CN); Peter Chee-Keung Chung, Room 1505, Argyle Centre, 688 Nathan Road, Mongkok, Kowloon (HK)

( * ) Notice: Subject to any disclaimer, the term of this patent is extended or adjusted under 35 U.S.C. 154(b) by 0 days.

(21) Appl. No.: 09/810,213

(22) Filed: Mar. 19, 2001

(51) Int. Cl.⁷ .............................................. A61K 35/78
(52) U.S. Cl. ................................ 424/195.15; 435/254.1
(58) Field of Search .................... 424/195.15; 435/254.1

(56) References Cited

U.S. PATENT DOCUMENTS

| | | |
|---|---|---|
| 4,675,198 A | 6/1987 | Sevenants |
| 5,017,397 A | 5/1991 | Nguyen et al. |
| 6,111,108 A | 8/2000 | Lopez-Avila et al. |

OTHER PUBLICATIONS

Wasser, Solomon P. et al.; Therapeutic Effects of Substances Occurring in Higher Basidiomycetes Mushrooms: A Modern Perspective; Critical Reviews in Immunology, 1999, vol. 19, P 65–96.
Lin, Lee–Juian et al.; Separation of oxygenated triterpenoids from *Ganoderma lucidum* by high–performance liquid chromatography; Journal of Chromatography, 1987, vol. 410, P 195–200.
El–Mekkawy, Sahar et al.; Anti–HIV–1 and Anti–HIV–1–Protease Substances from *Ganoderma lucidum*; Phytochemistry, 1998, vol. 49, No. 6, P 1651–1657.
O'Neil, Carol E. et al.; Basidiospore Extracts: Evidence for Common Antigenic/Allergenic Determinants; Int. Archs Allergy appl. Immun., 1988, vol. 85, P 161–166.
Kim, Kug Chan et al.; *Ganoderma lucidum* extract protects DNA from strand breakage caused by hydroxyl radical and UV irradiation; International Journal of Molecular Medicine, 1999, vol. 4, P 273–277.
Min, Byung–Sun et al.; Triterpenes from the Spores of *Ganoderma lucidum* and Their Inhibitory Activity against HIV–1 Protease; Chem Pharm Bull, 1998, vol. 46(10), P 1607–1612
Kino et al.; An immunomodulating protein, Ling Zhi–8 (LZ–8) prevents insulitis in non–obese diabetic mice; Diabetologia, 1990, vol. 33, P 713–718.
Gengtao, Liu et al.; Some Pharamacological Actions of the Spores of *Ganoderma Lucidum* and the Mycelium of *Ganoderma Capense* (Lloyd) Teng Cultivated by Submerged Fermentation; Chinese Medical Journal, 1979, vol. 92(7), P 496–500.

*Primary Examiner*—Francisco Prats
*Assistant Examiner*—Susan D. Coe
(74) *Attorney, Agent, or Firm*—Fei-Fei Chao; Venable, Baetjer, Howard & Civiletti, LLP

(57) ABSTRACT

The present invention relates to a method for extracting the oleaginous substances from sporoderm-broken Ganoderma spores using SCF—$CO_2$. The method contains the steps of: (1) inducing germination of Ganoderma spores by incubating the spores in a nutritional solution; (2) activating the Ganoderma spores by placing the germination-induced spores in a well ventilated culture box kept at constant temperature and humidity; (3) breaking the Ganoderma spores by a mechanical means to obtain the sporoderm-broken spores; and (4) extracting the oleaginous substances from the sporoderm-broken spores using a supercritical fluid—carbon dioxide (SCF—$CO_2$) extraction method. The preferred supercritical conditions include 5 M to 60 M Pa of pressure; 32° C. to 85° C. of temperature; and 5 kg/h to 80 kg/h of flow capacity rate. The total extraction time in SCF—$CO_2$ is between 0.5 hour to 6 hour. The method produces approximately 37% by weight of oleaginous substances from the sporoderm-broken Ganoderma spores. These oleaginous substances are transparent and contain the special fragrance of Ganoderma spores. There is no trace of deposit, solvent residue, or oxidization in the oleaginous substances.

19 Claims, No Drawings

US 6,440,420 B1

METHOD FOR EXTRACTING OLEAGINOUS SUBSTANCES FROM GERMINATION-ACTIVATED *GANODERMA LUCIDUM* SPORES

FIELD OF THE INVENTION

The present invention relates to a method for extracting oleaginous substances from *Ganoderma lucidum* spores, which are germination-activated and epispore-broken. The extraction method involves the use of supercritical fluid carbon dioxide ("SCF—$CO_2$").

BACKGROUND OF THE INVENTION

Ganoderma (*Ganoderma lucidum* Leyss ex Fr. Karst) is a polyporous fungus. It belongs to the class of Basidiomycetes, the family of Polypolaceae, and the genus of Ganoderma. In Chinese folklore, Ganoderma has been regarded as a panacea, which is probably due to certain efficacy of Ganoderma in treating many diseases. Some of the known medicinal or therapeutic effects of Ganoderma include treating patients with chronic bronchitis, chronic viral hepatitis, coronary heart disease, granulocytopenia, chronic Keshan disease, neurasthenia, progressive muscular dystrophy, atrophic myotonia and certain neurological diseases (See e.g., Liu et al., *Chinese Medical Journal*, 92:496–500 (1979)). There are also reports on Ganoderma as anti-HIV agent (See e.g., El-Mekkawy et al., *Phytochemistry*, 49: 1651–1657 (1998); Min et al., *Chem. Pharm. Bull*, 46: 1607–1612 (1998)), or for having anti-tumor, cardiovascular, antiviral, antibacterial, antiparasitic, and immune modulating activities (See e.g., Wasser et al., Critical Review in Immunology, 19:65–96 (1999)).

There are two major types of compounds found in Ganoderma which have been shown to be associated with the medicinal or therapeutic effects of Ganoderma. They are the polysaccharide compounds and the terpenoids. The polysaccharide compounds are primarily water-soluble. The terpenoids are oleaginous substances and are generally insoluble in water.

The polysaccharide compounds isolated from Ganoderma include hetero-β-glucans and their protein complexes (such as xyloglucans and acidic β-glucan-containing uronic acid, dietary fibers, lectins). The polysaccharides found in Ganoderma have been reported to possess anti-tumor and immune modulating effects (See Wasser et al., supra).

The Ganoderma terpenoids contain a lanostane skeleton. They are classified into several groups based on their carbon numbers and state of oxidation (Komoda et al., *Chem. Pharm. Bull.*, 33:4829–4835 (1985)). These Ganoderma terpenoids include lanostanine-type triterpenoids (e.g., ganoderic acids A, B, $C_1$, $C_2$, $D_1$, $D_2$, $E_1$, $E_2$, F, G, H, I, J, $K_1$, $K_2$, L, Ma, Mb, Mc, Md, Me, Mf, Mg, Mi, Mj, Mk, Mn, N, O, P, Q, S, T, U, V, W, X, Y, and Z), 7-O-methylganoderic acid O, trideacetyl ganoderic acid T, ganoderenic acids A, B, C, D, E, F, G, H, I, ganolucidic acids A, B, C, D, and E, lucidenic acids A, B, C, $D_1$, $D_2$, $E_1$, $E_2$, F, G, H, I, J, K, L, M, ganoderiol type 1 (A, B, F) and type 2 (C, D, E, F, G, H, and I), ganoderal A and B, epoxyganoderiol A, B, C, lucidone A, B, C, furanoganoderic acid, and other terpenoid components. Ganoderma terpenoids (e.g., ganoderic acids R, T, U–Z) have been reported to inhibit growth of hepatoma cells in vitro (See Toth et al., *Tetrahedron Lett.*, 24:1081–1084 (1983)).

Ganoderma spores are tiny mist-like brown oval-shaped spores of (6~7) μm×(10~12) μm in sizes which are released at the pelius of mature *Ganoderma lucidum*. These spores contain the entire genetic materials and biological substances of Ganoderma. However, the wild Ganoderma spores are difficult to collect, particularly due to their short release period and low germination rate under unfavorable environmental conditions. Therefore, although it is known that the Ganoderma spores are of greater pharmaceutical values than the fruiting bodies of Ganoderma, due to difficulties associated with the collection of the Ganoderma spores, most of the studies on Ganoderma are conducted using the fruiting bodies of Ganoderma.

The biological substances within the Ganoderma spores which give rise to the therapeutic effects of Ganoderma are stored within the double-layered epispores of *Ganoderma lucidum*. However, these epispores have compact structure, which are extremely rigid and resilient. Therefore, it is very difficult to break-open the epispore layers of the Ganoderma spores and release the biological substances therein using conventional extraction methods.

There have been reports on methods for breaking the epispores of Ganoderma spores. For example, Japanese Patent No. JP52041208 discloses an extraction method for breaking Ganoderma spores using mechanical force. Chinese Patent No. CN1134306 teaches a method for breaking the sporoderm of the Ganoderma spores by soaking the spores in water, followed by microwave-heating. Chinese Patent No. CN1165032 teaches a method for breaking the cell wall of *Ganoderma lucidum* spores by digesting the spores with skin-dissolving enzymes such as lysozyme, snail enzyme, cellulase, or hemicellulase, followed by ultrasonic breakage of the cell walls at 20–50° C. However, these methods use a mixed batch of spores collected from different stages of the Ganoderma lifecycle. It is known that the spores at different stages of the lifecycle produce different kinds and/or proportions of the biological substances, which may or may not possess the high level of therapeutic effects as expected. Therefore, the sporoderm-broken spores produced by these methods display inconsistent results and their respective medicinal effects vary.

There have also been reports on isolation or separation of the oleaginous substances (e.g., the terpenoids) from Ganoderma, most involving the use of organic solvents. For example, Min et al., *Chem. Pharm. Bull.*, supra, disclose the isolation of lanostane-type triterpenes using column chromatography of a $CHCl_3$-soluble fraction of the methanol extract of the Ganoderma spores. Lin et al., *J. Chromatography*, 410: 195–200 (1987) disclose the separation of oxygenated triterpenoids from *Ganoderma lucidum* by high-performance liquid chromatography of a methanolic extract of *Ganoderma lucidum*. These methods are unsatisfactory due to complex extraction procedures and low yield of the oleaginous substances.

In the present invention, a method for extracting the oleaginous substances from Ganoderma spores is provided. The Ganoderma spores to be used in the present invention are germination-activated to ensure that the biological substances are maximally produced. The epispores of the germination-activated Ganoderma spores are broken by a mechanical means to release the biological substances. Finally, the oleaginous substances of the biological substances are separated by a supercritical fluid carbon dioxide (SCF—$CO_2$) extraction method. The present invention has the advantage of producing high yield of oleaginous substances from Ganoderma (i.e., the yield of the oleaginous substances is about 37% by weight of the entire biological substances released from Ganoderma). The oleaginous substances isolated based on the present method retain the special fragrance of Ganoderma and are without solvent residue and strange odor.

SUMMARY OF THE INVENTION

The present invention provides a method for extracting the oleaginous substances from the sporoderm-broken Ganoderma spores using a supercritical fluid carbon dioxide ($SCF-CO_2$) extraction method. The Ganoderma spores are germination-activated and sporoderm-broken.

To obtain the germination-activated Ganoderma spores, the Ganoderma spores are first soaked in a nutritional solution which is suitable for inducing germination. The nutritional solution for germination purpose includes, but is not limited to, an immersed solution of Ganoderma fruiting body, a biotin solution, water, and an immersed solution of Ganoderma mycelium. The immersed solution of Ganoderma fruiting body or Ganoderma mycelium is preferably 0.5 to 25% by weight; the preferred biotin solution is 0.1 to 0.5% by weight. The ratio between the volume of the nutritional solution and the weight of Ganoderma spores is about 0.01 to 5 times. The preferred soaking time is between 10 minutes to 10 hours. The preferred soaking temperature is between 16° C. and 43° C.

The germination-induced Ganoderma spores are activated by placing the soaked Ganoderma spores in a well-ventilated culture box. The preferred relative humidity is 60% to 98%. The preferred temperature is 16° C. to 43° C. The preferred activation period is between 10 minutes and 24 hours.

The breakage of the epispores of the Ganoderma spores can be achieved by applying a mechanical means to the spores. The preferred mechanical means includes, without limitation, micronization, ultra-high-speed airstream, scissor-cut/grinding, and ultra-high pressure microstream. It is optional to incubate the germination-activated Ganoderma spores with enzymes such as chitinase and/or cellulase to soften the cell walls of the spores before applying the mechanical means to the spores.

The extraction of oleaginous substances from the germination activated and sporoderm-broken Ganoderma spores is carried out by a supercritical fluid carbon dioxide ($SCF-CO_2$) extraction method. The method includes the steps of: (1) placing the spores in a pressure vessel; (2) contacting $SCF-CO_2$ with the spores in the pressure vessel; and (3) depressurizing the pressure vessel to collect the oleaginous substances from the Ganoderma spores. The pressure in the pressure vessel is preferably between 5 M Psia (Pa) to 60 M Pa. The temperature in the pressure vessel is preferably maintained at 32° C. to 85° C. The preferred flow capacity rate of the pressure vessel is between 5 kg/h and 80 kg/h. The preferred extraction time is between 30 minutes and 6 hours.

Optionally, the sporoderm-broken Ganoderma spores are mixed with a carrier, such as water or 85% to 100% ethanol, before being placed in the pressure vessel. The preferred ratio of the carrier to the Ganoderma spores is 2% to 200% by weight. The oleaginous substances are preferred to be separated from the carrier by centrifugation.

The $SCF-CO_2$ extraction method produces oleaginous substances from the Ganoderma spores, which are about 37% of the total weight of the Ganoderma spores. The oleaginous substances are transparent and contain a special fragrance of the Ganoderma spores. There is no trace of deposit, solvent residue, or oxidization in the oleaginous substances.

The oleaginous substances extracted from the sporoderm-broken Ganoderma spores possess medicinal effects, which include, without limitation, anti-tumor, anti-HIV or -HBV, and anti-immunological disorders. They can be used in treating patients with tumors, HIV or HBV infection, and immunological disorders.

DETAILED DESCRIPTION OF THE INVENTION

The present invention provides an extraction method to isolate and separate the oleaginous substances from Ganoderma spores by using an $SCF-CO_2$. The amount of the oleaginous substances produced by this method constituted about 37% of the total weight of the spores. In addition, the oleaginous substances produced by this method were well preserved in its natural state (i.e., free of solvent residue and strange odor). The strange odor is an indication that the oleaginous substances have been oxidized.

Conventionally, the ways to extract or separate substances in a mixture include distillation and solvent extraction. Distillation separates the substances in a mixture according to the boiling characteristics of each substance. Solvent extraction separates the substances in a mixture according to the hydrophilic and lipophilic property of each substance. Distillation cannot be used when the substances to be separated are thermally unstable. Solvent extraction has limited utility when the substances to be separated are so similar in solubility that efficient separation cannot be obtained.

Supercritical fluids (SCFs) technology is a viable alternative to the conventional extraction methods. SCFs are often referred to as dense gases. Technically, an SCF is a gas existing above its critical temperature and critical pressure. When a gas is compressed above its critical temperature, densities increase dramatically. Therefore, under a given set of conditions, an SCF may possess the density of a liquid while maintaining the diffusivity of a gas.

Each gas has a critical pressure (Pc) and a critical temperature (Tc), above each of which a supercritical fluid state is attained. Solvent properties of such SCFs have been found to be a complex function of the fluid density which in turn is a complex function of temperature and pressure. Thus, by varying the temperature and pressure of a supercritical fluid, extractions and precipitations can be carried out.

Carbon dioxide has proven to be a particularly advantageous gas to use in SCF extractions because it possesses good solvent properties and has low chemical reactivity and toxicity. In addition, carbon dioxide is not flammable, is inexpensive and may be readily recycled, and leaves no undesirable residues in the precipitates. Carbon dioxide has a Pc of 73.8 bar, a Tc of 31.1° C., and a density at the Pc and Tc of 0.468 g/cc.

By use of $SCF-CO_2$, any material in a mixture which exists in or which can be converted to a physical state that is permeable to the carbon dioxide under supercritical conditions will be dissolved in the carbon dioxide and be separated from the mixture. The principle behind the $SCF-CO_2$ extraction method is that under the high pressures required for extraction with gases in the supercritical fluid, the solubility of many organic compounds is increased. This, combined with the greater diffusivity of supercritical fluid over conventional solvents, results in a more rapid mass transfer through the material to be extracted, and thus a faster rate of extraction. Supercritical fluid gases have the ability to selectively dissolve and extract organic species from organic mixtures, organic/aqueous mixtures, organic/inorganic matrices, and lipophilic/hydrophilic matrices. Theoretically, the higher the pressure, the greater the efficiency of the extraction. Essentially, most or all of the oleaginous substances (with low solubility in water) in the Ganoderma spores should be dissolved in the carbon dioxide.

The tiny spores of *Ganoderma lucidum* has an extremely hard and resilient, double-layered epispore. In the wild, the germination of the spores of *Ganoderma lucidum* is relatively slow and their germination rate is extremely low. It takes about 24 to 48 hours for the germ tubes of the spores start to sprout under proper conditions, and the capillitia start to form branches after 72 hours, with a germination rate of only 3–15%.

When the tiny spores of *Ganoderma lucidum* were extracted under SCF—$CO_2$, only approximately 3.5% of the oleaginous substances were recovered.

In order to maximize the production of oleaginous substances from *Ganoderma lucidum*, a germination-activation procedure was designed. This procedure was followed by a sporoderm-breaking process to break open the cell walls of the Ganoderma epispores. Finally, the germination-activated, sporoderm-broken Ganoderma spores were extracted under the SCF—$CO_2$ to separate the oleaginous substances from the spores.

It was noted that when the dormant Ganoderma spores were germination-activated, the production rate of the biological substances in the spores reached the maximum. These biological substances contain, inter alia, active genes and promoters, active enzymes, sterols, cytokines, interferons, lactone A, ganoderma acid A, triterpenes, polysaccharides, vitamins, superoxide dismutases (SOD), glycoproteins, etc. These biological substances demonstrate superb medicinal effects, particularly on stimulating and modulating the nervous system and the immune system. Also, it was noted that during the germination-activation period, the resilience of the epispore significantly decreased, which in turn increased the penetration rate of the cell walls of the epispore.

The results of the animal and clinical studies on the effect of germination-activation showed that the biological substances produced from the germination-activated Ganoderma spores demonstrated inhibitory effects on liver cancer by suppressing the activity of telomerase in the hepatic cancerous tissue. These biological substances also demonstrated therapeutic effects on HBV infection. Additionally, when the germination-activated Ganoderma spores were given to animals, the results showed that the sporoderm-unbroken spores had an anti-tumor rate of 23.2%, which was substantially lower than the sporoderm-broken spores, which had an anti-tumor rate of 86.1%.

The extraction method of the present invention is described as follows:

1. Collection of Ganoderma Spores. Mature and plump Ganoderma spores were collected at the appropriate release time from *Ganoderma lucidum* cultured on log. It was advantageous to culture Ganoderma on log, because the spores thus produced were fresher and more nutritious and the penetration/ breaking rate for the epispores was much higher.

2. Induction of Ganoderma Spores Germination. The selected spores were soaked in a nutritional solution which could be distilled water, a saline solution, a solution which had been immersed with the fruiting bodies of Ganoderma or the mycelia of Ganoderma. The purpose of soaking the spores in the nutritional solution was to enable and accelerate the germination of the spores. Examples of the nutritional solution include 0.5~25% by weight of the immersion solution of the Ganoderma fruiting bodies or mycelia, 0.1~0.5% by weight of the biotin solution, etc. The nutritional solution was about 0.01~5 times of the weight of the Ganoderma spores. The soaking time was about 10 minutes~8 hours. The temperature was about 16~43° C.

3. Activation of the Germinated Ganoderma Spores. To activate the germinated Ganoderma spores, the soaked spores were removed from the nutritional solution and excess solution was allowed to drip. The soaked spores were then placed in a well-ventilated culture box which was kept in constant temperature and humidity. The relative humidity in the culture box was maintained at about 60~98%. The temperature of the culture box was maintained at about 16~48° C. The time for activating the spores was about 10 minutes~24 hours.

4. Penetration/Breakage of the Epispores. After the Ganoderma spores were germination-activated, the spores were further broken by a mechanical means. Examples of the mechanical means used to break the spores include micronization, roll-pressing, or scissor-cut/grinding, microstream-impact crushing, ultra-high-speed airstream impact crushing, ultra-high pressure microstream crushing, ultra-low temperature crushing etc.

Before breaking the epispores, it was optional to treat the spores with enzymes such as chitinase and cellulase to soften the cell walls of the epispores. The enzyme-treated spores could be separated from the reaction mixture by centrifugation at about 3,000~30,000 rpm or ultra-filtration using a filter with about 10,000 molecular weight cut-off.

5. Extraction of Oleaginous Substances with SCF—$CO_2$. The extraction of the oleaginous substances from the sporoderm-broken spores was conducted in an SCF—$CO_2$ extracting apparatus, which included a $CO_2$ source, a compressor, a heat exchanger, a pressure regulator, and a pressure vessel. Alternatively, any conventional supercritical fluid extraction equipment which contains an extractor (i.e., the pressure vessel) and a separator would also be suitable for the extraction. To operate, the sporoderm-broken spores were placed in the pressure vessel. The carbon dioxide was flowed through the compressor and heat exchanger to achieve greater than supercritical temperature and pressure, and then flowed through the spores in the pressure vessel. The SCF was then removed from the pressure vessel and depressurized to evaporate the carbon dioxide. The supercritical pressure used in the present method was about 5~60 M Pa. The supercritical temperature was in the present method was about 32~85° C. The flow volume rate of $CO_2$ was about 5~80 kg/h. The extraction time was about 0.5~6 hours.

It was optional to add a carrier to the spores between initiating the SCF—$CO_2$ extraction. Examples of the carrier include water or 85~100% of ethanol. The ratio of the carrier to the spores was about 2~200% (v/w). When the carrier was added to the spores, the oleaginous substances could be separated from the rest of the spores by centrifugation at about 3,000~30,000 rpm.

The following examples are intended only to further illustrate the invention and are not intended to limit the scope of the present invention that is defined by the examples. Reasonable variations, such as those occur to reasonable artisan, can be made herein without departing from the scope of the present invention.

EXAMPLE 1

The oleaginous substances from the Ganoderma spores were extracted according to the method shown below:

1. One hundred (100) kg of mature and plump Ganoderma spores were carefully selected.

2. A nutritional solution containing 2 kg of 5% immersion solution of Ganoderma fruiting bodies and 150 kg of saline (0.15 M NaCl) was added to the spores. The spores were soaked in the nutritional solution for 6 hours at 32° C.

3. The soaked Ganoderma spores were removed from the nutritional solution and placed into a well-ventilated culture box which was kept at constant temperature of 34° C. and relative humidity of 90%. The spores were maintained in the culture box for 3 hours. Under such condition, the germination rate of the spores was 95% and the cell walls of the germination-activated spores showed clear signs of softening.

4. The germination-activated Ganoderma spores were micronized. The spores were monitored under the microscope. The penetration/breaking rate of the epispores reached 99.6% after this treatment.

5. The epispore-broken Ganoderma spores were placed in the pressure vessel of the extraction apparatus for SCF—$CO_2$. The supercritical pressure was kept at 45 M Pa and the supercritical temperature was at 53° C. The flow volume rate of $CO_2$ was kept at 60 kg/h. The total extraction time was 1.5 hours.

Results:

This method produced about 37 kg of oleaginous substances (which constituted approximately 37% by weight of the spores). The oleaginous substances were transparent and contained the special fragrance of Ganoderma spores, an indication that the oleaginous substances were not oxidized. There was no trace of deposit or solvent residue in the oleaginous substances.

EXAMPLE 2

The oleaginous substances from the Ganoderma spores were extracted according to the method shown below:

1. One hundred (100) kg of mature and plump Ganoderma spores were carefully selected.

2. A nutritional solution containing 20 kg of 1% biotin solution and 250 kg of distilled water was added to the spores. The spores were soaked in the nutritional solution for 3 hours at 43° C.

3. The soaked Ganoderma spores were removed from the nutritional solution and placed into a well-ventilated culture box which was kept at temperature of 18° C. and relative humidity of 60%. The spores were maintained in the culture box for 24 hours. Under such condition, the germination rate of the spores was 95% and the cell walls of the germination-activated spores showed clear signs of softening.

4. An enzyme mixture containing 5 g of chitinase, 10 g of cellulose, and 150 kg of distilled water (at pH 6.8) was added to and reacted with the spores. The reaction was performed at the temperature of 43° C. for 1.5 hours. At the end of the reaction, the epispores had lost their resilience.

5. The spores were micronized with crushing. The spores were monitored under the microscope. The penetration/breaking rate of the epispores reached 99.6% after this treatment. The sporoderm-broken spores were separated from the enzyme mixture by centrifugation at 3,000 rpm.

6. The spores were then placed in the pressure vessel of the extraction apparatus for SCF—$CO_2$. Ten (10) kg of 90% ethanol were added to the spores as a carrier. The supercritical pressure was kept at 40 M Pa and the supercritical temperature was at 32° C. The flow volume rate of $CO_2$ was kept at 15 kg/h. The total extraction time was 5 hours.

7. After $SCF_2$ extraction, the oleaginous substances were separated from the carrier by centrifugation at 6,000 rpm.

Results:

This method produced about 36.9 kg of oleaginous substances (which constituted approximately 36.9% by weight of the spores). The oleaginous substances were transparent and contained the special fragrance of Ganoderma spores, an indication that the oleaginous substances were not oxidized. There was no trace of deposit or solvent residue in the oleaginous substances.

EXAMPLE 3

The oleaginous substances from the Ganoderma spores were extracted according to the method shown below:

1. One hundred (100) kg of mature and plump Ganoderma spores were carefully selected.

2. A nutritional solution containing 200 kg of distilled water was added to the spores. The spores were soaked in this solution for 8 hours at 16° C.

3. The soaked spores were removed from the nutritional solution and placed in a well-ventilated culture box which was kept at temperature of 48° C. and relative humidity of 98% for 10 minutes. Under such condition, the germination rate of the spores was 95% and the cell walls of the germination-activated spores showed clear signs of softening.

4. An enzyme mixture containing 10 g of chitinase, 20 g of cellulose, and 200 kg of distilled water (at pH 6.8) was added to and reacted with the spores. The reaction was performed at the temperature of 38° C. for 3.0 hours. At the end of the reaction, the epispores had lost their resilience.

5. The sporoderm of the spores were broken by rolling/pressing with crushing. The spores were monitored under the microscope. The sporoderm-broken spores were separated from the enzyme mixture by ultra-filtration.

6. The spores were then placed in the pressure vessel of the extraction apparatus for SCF—$CO_2$. The supercritical pressure was kept at 60 M Pa and the supercritical temperature was at 48° C. The flow volume rate of $CO_2$ was kept at 5 kg/h. The total extraction time was 4.5 hours.

Results:

This method produced about 36.9 kg of oleaginous substances (which constituted approximately 36.9% by weight of the spores). The oleaginous substances were transparent and contained the special fragrance of Ganoderma spores, an indication that the oleaginous substances were not oxidized. There was no trace of deposit or solvent residue in the oleaginous substances.

EXAMPLE 4

The oleaginous substances from the Ganoderma spores were extracted according to the method shown below:

1. One hundred (100) kg of mature and plump Ganoderma spores were carefully selected.

2. A nutritional solution containing 10 kg of 0.5% of immersed solution of Ganoderma fruiting bodies, 10 kg of 0.1% biotin solution, and 200 kg of distilled water was added to the spores. The spores were soaked in this solution for 30 minutes at 25° C.

3. The soaked spores were removed from the nutritional solution and placed in a well-ventilated culture box which was kept at temperature of 16° C. and relative humidity of 80% for 24 hours. Under such condition, the germination rate of the spores was 95% and the cell walls of the germination-activated spores showed clear signs of softening.

4. Ultra-high-speed airstream was used to break the epispores of the spores. The broken spores were monitored under a microscope. About 99.6% of the spores were broken under this condition.

5. The spores were then placed in the pressure vessel of the extraction apparatus for SCF—$CO_2$. Fifty (50) kg of 100% ethanol were added as a carrier. The supercritical pressure was kept at 10 M Pa and the supercritical temperature was at 85° C. The flow volume rate of $CO_2$ was kept at 80 kg/h. The total extraction time was 6 hours.

6. After SCF—$CO_2$ extraction, the oleaginous substances were separated from the carrier by centrifugation at 20,000 rpm.

Results:

This method produced about 37 kg of oleaginous substances (which constituted approximately 37% by weight of the spores). The oleaginous substances were transparent and contained the special fragrance of Ganoderma spores, an indication that the oleaginous substances were not oxidized. There was no trace of deposit or solvent residue in the oleaginous substances.

EXAMPLE 5

The oleaginous substances from the Ganoderma spores were extracted according to the method shown below:

1. One hundred (100) kg of mature and plump Ganoderma spores were carefully selected.

2. A nutritional solution containing 50 kg of 5% of immersed solution of Ganoderma mycelia and 5 kg of 0.1% biotin solution was added to the spores. The spores were soaked in this solution for 5 hours at 38° C.

3. The soaked spores were removed from the nutritional solution and placed in a well-ventilated culture box which was kept at temperature of 30° C. and relative humidity of 70% for 1.5 hours. Under such condition, the germination rate of the spores was 95% and the cell walls of the germination-activated spores showed clear signs of softening.

4. An enzyme mixture containing 20 g of chitinase and 180 kg of distilled water (at pH 6.4) was added to and reacted with the spores. The reaction was performed at the temperature of 38° C. for 4.0 hours. At the end of the reaction, the epispores had lost their resilience.

5. The spores were broken by scissor-cutting/ grinding. The broken spores were monitored under a microscope. About 99.6% of the spores were broken under this condition. The sporoderm-broken spores were separated from the enzyme mixture by centrifugation at 15,000 rpm.

6. The spores were then placed in the pressure vessel of the extraction apparatus for SCF—$CO_2$. Fifty (50) kg of distilled water were added as a carrier. The supercritical pressure was kept at 55 M Pa and the supercritical temperature was at 55° C. The flow volume rate of $CO_2$ was kept at 42 kg/h. The total extraction time was 2 hours.

7. After SCF—$CO_2$ extraction, the oleaginous substances were separated from the carrier by centrifugation at 20,000 rpm.

Results:

This method produced about 37 kg of oleaginous substances (which constituted approximately 37% by weight of the spores). The oleaginous substances were transparent and contained the special fragrance of Ganoderma spores, an indication that the oleaginous substances were not oxidized. There was no trace of deposit or solvent residue in the oleaginous substances.

EXAMPLE 6

The oleaginous substances from the Ganoderma spores were extracted according to the method shown below:

1. One hundred (100) kg of mature and plump Ganoderma spores were carefully selected.

2. A nutritional solution containing 5 kg of 20% of immersed solution of Ganoderma fruiting bodies and 150 kg of distilled water was added to the spores. The spores were soaked in this solution for 2 hours at 28° C.

3. The soaked spores were removed from the nutritional solution and placed in a well-ventilated culture box which was kept at temperature of 40° C. and relative humidity of 65% for 3 hours. Under such condition, the germination rate of the spores was 95% and the cell walls of the germination-activated spores showed clear signs of softening.

4. The epispores of the spores were broken by micronization. The broken spores were monitored under a microscope. About 99.7% of the spores were broken under this condition.

5. The spores were then placed in the pressure vessel of the extraction apparatus for SCF—$CO_2$. Two hundred (200) kg of 95% ethanol were added as a carrier. The supercritical pressure was kept at 55 M Pa and the supercritical temperature was at 68° C. The flow volume rate of $CO_2$ was kept at 70 kg/h. The total extraction time was 2 hours.

7. After SCF—$CO_2$ extraction, the oleaginous substances were separated from the carrier by centrifugation at 20,000 rpm.

Results:

This method produced about 37 kg of oleaginous substances (which constituted approximately 37% by weight of the spores). The oleaginous substances were transparent and contained the special fragrance of Ganoderma spores, an indication that the oleaginous substances were not oxidized. There was no trace of deposit or solvent residue in the oleaginous substances.

EXAMPLE 7

The oleaginous substances from the Ganoderma spores were extracted according to the method shown below:

1. One hundred (100) kg of mature and plump Ganoderma spores were carefully selected.

2. A nutritional solution containing 20 kg of 25% of immersed solution of Ganoderma mycelia and 150 kg of distilled water was added to the spores. The spores were soaked in this solution for 6 hours at 22° C.

3. The soaked spores were removed from the nutritional solution and placed in a well-ventilated culture box which was kept at temperature of 26° C. and relative humidity of 75% for 4 hours. Under such condition, the germination rate of the spores was 95% and the cell walls of the germination-activated spores showed clear signs of softening.

4. An enzyme mixture containing 20 g of cellulose and 250 kg of distilled water (at pH 5.6) was added to and reacted with the spores. The reaction was performed at the temperature of 45° C. for 2 hours. At the end of the reaction, the epispores had lost their resilience.

5. The spores were broken by rolling/pressing. The broken spores were monitored under a microscope. About 99.7% of the spores were broken under this condition. The sporoderm-broken spores were separated from the enzyme mixture by centrifugation at 15,000 rpm.

6. The spores were then placed in the pressure vessel of the extraction apparatus for SCF—$CO_2$. The supercritical pressure was kept at 55 M Pa and the supercritical temperature was at 70° C. The flow volume rate of $CO_2$ was kept at 60 kg/h. The total extraction time was 0.5 hours.

Results:

This method produced about 36.9 kg of oleaginous substances (which constituted approximately 36.9% by weight of the spores). The oleaginous substances were transparent and contained the special fragrance of Ganoderma spores, an indication that the oleaginous substances were not oxidized. There was no trace of deposit or solvent residue in the oleaginous substances.

EXAMPLE 8

The oleaginous substances from the Ganoderma spores were extracted according to the method shown below:

1. One hundred (100) kg of mature and plump Ganoderma spores were carefully selected.

2. A nutritional solution containing 20 kg of 1% of biotin solution and 150 kg of distilled water was added to the spores. The spores were soaked in this solution for 2 hours at 40° C.

3. The soaked spores were removed from the nutritional solution and placed in a well-ventilated culture box which was kept at temperature of 18° C. and relative humidity of 88% for 12 hours. Under such condition, the germination rate of the spores was 95% and the cell walls of the germination-activated spores showed clear signs of softening.

4. The epispores of the spores were broken by scissor-cut/grinding. The broken spores were monitored under a microscope. About 99.9% of the spores were broken under this condition.

5. The spores were then placed in the pressure vessel of the extraction apparatus for SCF—$CO_2$. Seventy (70) kg of 95% ethanol were added as a carrier. The supercritical pressure was kept at 10 M Pa and the supercritical temperature was at 38° C. The flow volume rate of $CO_2$ was kept at 18 kg/h. The total extraction time was 4 hours.

6. After SCF—$CO_2$ extraction, the oleaginous substances were separated from the carrier by centrifugation at 15,000 rpm.

Results:

This method produced about 37 kg of oleaginous substances (which constituted approximately 37% by weight of the spores). The oleaginous substances were transparent and contained the special fragrance of Ganoderma spores, an indication that the oleaginous substances were not oxidized. There was no trace of deposit or solvent residue in the oleaginous substances.

EXAMPLE 9

The oleaginous substances from the Ganoderma spores were extracted according to the method shown below:

1. One hundred (100) kg of mature and plump Ganoderma spores were carefully selected.

2. A nutritional solution containing 250 kg of distilled water was added to the spores. The spores were soaked in this solution for 10 hours at 34° C.

3. The soaked spores were removed from the nutritional solution and placed in a well-ventilated culture box which was kept at temperature of 31° C. and relative humidity of 80% for 2 hours. Under such condition, the germination rate of the spores was 95% and the cell walls of the germination-activated spores showed clear signs of softening.

4. An enzyme mixture containing 10 g of chitinase and 250 kg of distilled water (at pH 6.8) was added to and reacted with the spores. The reaction was performed at the temperature of 44° C. for 2 hours. At the end of the reaction, the epispores had lost their resilience.

5. The spores were broken by micronization/pressing. The broken spores were monitored under a microscope. About 99.9% of the spores were broken under this condition. The sporoderm-broken spores were separated from the enzyme mixture by centrifugation at 30,000 rpm.

6. The spores were then placed in the pressure vessel of the extraction apparatus for SCF—$CO_2$. Two (2) kg of distilled water were added as a carrier. The supercritical pressure was kept at 14 M Pa and the supercritical temperature was at 45° C. The flow volume rate of $CO_2$ was kept at 12 kg/h. The total extraction time was 2 hours.

7. After SCF—$CO_2$ extraction, the oleaginous substances were separated from the carrier by centrifugation at 30,000 rpm.

Results:

This method produced about 36.8 kg of oleaginous substances (which constituted approximately 36.8% by weight of the spores). The oleaginous substances were transparent and contained the special fragrance of Ganoderma spores, an indication that the oleaginous substances were not oxidized. There was no trace of deposit or solvent residue in the oleaginous substances.

EXAMPLE 10

The oleaginous substances from the Ganoderma spores were extracted according to the method shown below:

1. One hundred (100) kg of mature and plump Ganoderma spores were carefully selected.

2. A nutritional solution containing 200 kg of saline solution was added to the spores. The spores were soaked in this solution for 6 hours at 22° C.

3. The soaked spores were removed from the nutritional solution and placed in a well-ventilated culture box which was kept at temperature of 34° C. and relative humidity of 75% for 5 hours. Under such condition, the germination rate of the spores was 95% and the cell walls of the germination-activated spores showed clear signs of softening.

4. The epispores of the spores were broken by ultra-high pressure microstream. The broken spores were monitored under a microscope. About 99.9% of the spores were broken under this condition.

5. The spores were then placed in the pressure vessel of the extraction apparatus for SCF—$CO_2$. Sixty five (65) kg of 85% ethanol were added as a carrier. The supercritical pressure was kept at 14 M Pa and the supercritical temperature was at 40° C. The flow volume rate of $CO_2$ was kept at 25 kg/h. The total extraction time was 1 hour.

6. After SCF-$CO_2$ extraction, the oleaginous substances were separated from the carrier by centrifugation at 8,000 rpm.

Results:

This method produced about 37 kg of oleaginous substances (which constituted approximately 37% by weight of the spores). The oleaginous substances were transparent and contained the special fragrance of Ganoderma spores, an indication that the oleaginous substances were not oxidized. There was no trace of deposit or solvent residue in the oleaginous substances.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A method for extracting oleaginous substances from spores of *Ganoderma lucidum* comprising:
   soaking Ganoderma spores in a nutritional solution to produce germination-induced Ganoderma spores;
   placing said germination-induced Ganoderma spores in a ventilated culture box until cell walls of said Ganoderma spores are softened to produce germination-activated Ganoderma spores;
   breaking sporoderm of said germination-activated Ganoderma spores by a mechanical means to obtain sporoderm-broken Ganoderma spores, and
   extracting oleaginous substances from said sporoderm-broken Ganoderma spores using a supercritical fluid-carbon dioxide (SCF—$CO_2$) extraction method.

2. The method according to claim 1, wherein said nutritional solution is at least one which is selected from the group consisting of an immersed solution of Ganoderma fruiting body, a biotin solution, water, and an immersed solution of Ganoderma mycelium.

3. The method according to claim 1, wherein said Ganoderma spores are soaked in said nutritional solution between 10 minutes and 10 hours.

4. The method according to claim 1, wherein said Ganoderma spores are soaked in said nutritional solution between 16° and 43° C.

5. The method according to claim 1, wherein said ventilated culture box is at relative humidity between 60% and 98%.

6. The method according to claim 1, wherein said ventilated culture box is at temperature between 16° C. and 48° C.

7. The method according to claim 1, wherein said germination-induced Ganoderma spores are placed in said ventilated culture box for between 10 minutes and 24 hours.

8. The method according to claim 1, wherein said mechanical means for breaking said sporoderm-broken Ganoderma spores is at least one selected from the group consisting of micronization, airstream, scissor-cutting, grinding, and pressure microstream.

9. The method according to claim 8, further comprising a step of digesting said germination-activated Ganoderma spores with at least an enzyme before applying said mechanical means.

10. The method according to claim 9, wherein said enzyme is at least one selected from the group consisting of chitinase and cellulase.

11. The method according to claim 1, wherein said SCF-$CO_2$ extraction method comprises:
    placing said sporoderm-broken Ganoderma spores in a pressure vessel;
    contacting SCF-$CO_2$ with said Ganoderma spores in said pressure vessel; and
    depressurizing said pressure vessel to collect said oleaginous substances from said sporoderm-broken Ganoderma spores.

12. The method according to claim 11, wherein said pressure vessel is maintained at a pressure between 5 M Psia (Pa) to 60 M Pa.

13. The method according to claim 11, wherein said pressure vessel is maintained at a temperature of 32° C. to 85° C.

14. The method according to claim 11, wherein said pressure vessel is maintained at a flow volume rate of 5 kg/h to 80 kg/h.

15. The method according to claim 11, wherein said extraction time is between 30 minutes and 6 hours.

16. The method according to claim 11, wherein said sporoderm-broken Ganoderma spores are mixed with a carrier before placed in said pressure vessel.

17. The method according to claim 16, wherein said carrier is 85% to 100% ethanol (vol/vol) or water.

18. The method according to claim 16, wherein said carrier and said Ganoderma spores are at a weight ratio of 2% to 200%.

19. The method according to claim 16, further comprising a step of:
    separating said oleaginous substances from said carrier by centrifugation.

* * * * *